(12) United States Patent
Furuichi (10) Patent No.: US 9,033,890 B2
(45) Date of Patent: May 19, 2015

(54) OPTICAL COHERENCE TOMOGRAPHIC IMAGE FORMING APPARATUS AND CONTROL METHOD THEREOF

(75) Inventor: Junya Furuichi, Isehara (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 306 days.

(21) Appl. No.: 13/436,402

(22) Filed: Mar. 30, 2012

(65) Prior Publication Data

US 2012/0253185 A1  Oct. 4, 2012

(30) Foreign Application Priority Data

Mar. 31, 2011 (JP) ................................. 2011-078550

(51) Int. Cl.
*A61B 5/05* (2006.01)
*A61B 5/00* (2006.01)
*A61B 8/00* (2006.01)

(52) U.S. Cl.
CPC ............. *A61B 5/0066* (2013.01); *A61B 8/4461* (2013.01); *A61B 5/0084* (2013.01); *A61B 2560/0266* (2013.01); *A61B 2562/0233* (2013.01)

(58) Field of Classification Search
CPC ... A61B 5/0062; A61B 5/0066; A61B 8/4461
USPC .................. 600/467, 118, 137, 466
See application file for complete search history.

(56) References Cited

U.S. PATENT DOCUMENTS

2007/0232891 A1  10/2007  Hirota
2007/0232892 A1  10/2007  Hirota
2009/0073454 A1 *  3/2009  Ozawa .......................... 356/477

FOREIGN PATENT DOCUMENTS

EP           1 839 569 A2    10/2007
JP           2007-267867 A   10/2007

OTHER PUBLICATIONS

Extended European Search Report issued on Jul. 18, 2012, by the European Patent Office in corresponding European Patent Application No. 12161166.9-526. (6 pages).

* cited by examiner

*Primary Examiner* — Elmer Chao
(74) *Attorney, Agent, or Firm* — Buchanan Ingersoll & Rooney PC (57) ABSTRACT

An optical coherent tomographic image forming apparatus includes: a first switch for instructing rotation of the optical deflection unit at a first speed; a second switch for instructing rotation of the optical deflection unit at a second speed which is higher than the first speed; and a driving controller which drives the optical deflection unit rotationally at the first speed in case of detecting instruction operation of the first switch and which changes the rotation speed of the optical deflection unit to the second speed, in case of detecting instruction operation of the second switch, under the condition that the optical deflection unit rotates at the first speed when the second switch is instructionally operated.

3 Claims, 7 Drawing Sheets

OPTICAL COHERENCE TOMOGRAPHIC IMAGE FORMING APPARATUS AND CONTROL METHOD THEREOF

CROSS REFERENCES TO RELATED APPLICATIONS

This application contains subject matter related to Japanese Patent Application JP2011-078550 filed in the Japanese Patent Office on Mar. 31, 2011, the entire content of which is incorporated herein by reference.

FIELD OF THE INVENTION

The present invention relates to an optical coherence tomographic image forming apparatus and a control method thereof.

BACKGROUND DISCUSSION

Medical care is performed inside a blood vessel depending on a highly functional catheter such as a balloon catheter, a stent and the like. For this medical care, it has been becoming popular to use an imaging apparatus for diagnosis such as an optical coherence tomography (OCT) apparatus and the like for a diagnosis before operation or a follow-up confirmation after operation.

This imaging apparatus for diagnosis includes an optical lens at the distal end and further, includes a catheter installed with an optical fiber attached with an optical mirror. Then, a radial scan is carried out by inserting the catheter thereof inside a blood vessel of a patient, by illuminating light onto the blood vessel wall through the optical mirror while rotating the optical mirror and by light-receiving the reflected light again from a biological tissue through the optical mirror thereof, and a cross-sectional image of the blood vessel is to be constructed based on the obtained reflected light. Also, for an improved type OCT apparatus, there has been developed an optical frequency domain imaging (OFDI) apparatus.

The basic principle of the optical coherence tomographic diagnostic apparatus lies in that the light outputted from a light source inside the apparatus is divided into a measurement light and a reference light, and the measurement light is emanated through the optical mirror of the abovementioned optical fiber. Then, a scattering light reflected by the biological tissue is light-received through the same optical fiber, there is obtained an interference light with respect to the reference light which is reflected by going through a known distance, a tomographic image of the biological tissue (blood vessel) in the vicinity of the catheter is to be obtained from the intensity thereof. An example is disclosed in Japanese unexamined patent publication No. 2007-267867.

In particular, in case of the optical frequency domain imaging apparatus, it is possible, by sweeping the emanated optical wavelength repeatedly within a predetermined range, to obtain reflection-intensity distribution in the depth direction, in which the measurement light and the reference light are referenced to a same point, from the frequency distribution of the interference light obtained without handling the optical path length of the reference light.

SUMMARY

In case of the optical frequency domain imaging apparatus, the rotation speed of the mirror inside the catheter is made higher than it was before in order to heighten the resolution of the diagnosis image thereof. However, on the other hand, caused by the fact that the rotation speed is heightened, there arises such a problem as occurrence of its frictional heat. As mentioned above, since the catheter is an object inserted into the inside of a blood vessel, the less the influence of the frictional heat with respect to biological tissue is the better the result is. Also, the risk of breakdown is heightened by rotating the mirror at a high speed. Therefore, when rotating the mirror at a high speed, an upper limit is provided for a period during which the high speed rotation thereof is continued. Also, it is necessary for the timing of rotating the mirror at a high speed to match with the timing of carrying out the scan for obtaining the tomographic image of the targeted blood vessel region.

On the other hand, it is also required to judge whether or not the catheter is positioned at the measurement region for obtaining the tomographic image and/or to carry out a confirmation process as to whether or not the mirror rotates normally or the like. In this confirmation process, it is sufficient if a rough tomographic image of the blood vessel can be obtained and it is enough if it can be confirmed, by watching the image thereof, whether or not the mirror rotates normally, so that there is no problem even if the rotation speed of the mirror on an occasion thereof is in a low-speed rotation in which the influence of frictional heat can be ignored.

From the consideration mentioned above, the inventor here developed a conclusion about setting the rotation speed of the mirror into two stages. But the inventor here also became aware of the fact that there is a further problem in the case of providing an operation switch for simply instructing the high speed rotation and the low speed rotation respectively as desired. That is a problem in case of having instructed a high speed rotation by an erroneous operation. In a case in which the timing of instructing a scan for actually obtaining a tomographic image is near the continuation time-limit of the high speed rotation while not being aware of the fact that a high speed rotation has been instructed by an erroneous operation, the continuation time-limit is reached before the scan is completed and it happens that the measurement becomes invalid. Also, caused by the fact that a high speed rotation has been employed until the edge of the continuation time-limit, at that time point, the catheter becomes relatively in a high temperature. Therefore, it is desired, for the instruction of the high speed rotation again, to wait until there elapses a certain time period during which the temperature lowers adequately.

Consequently, the disclosed here is an optical coherence tomographic diagnostic apparatus configured to avoid an operation error involving the rotation speed of the mirror portion as mentioned above, and which it makes it possible to carry out a scan superior in operability.

The optical coherence tomographic image forming apparatus comprising a light source; an optical divider configured to divide a light outputted from the light source into a measurement light and a reference light; an optical probe insertable inside a body lumen and comprising an optical deflection unit provided at a distal end of the optical probe, the optical probe configured to emit the measurement light to the biological tissue and receive a reflected light; a drive unit configured to rotate the optical deflection unit centering around the axis thereof into the optical probe; and a signal processing unit configured to generate a cross-sectional image inside a biological tissue based on the light intensity of a interference light which is obtained from the reflected light and the reference light. The drive unit comprises: a first switch operable to instruct rotation of the optical deflection unit at a first speed; a second switch operable to instruct rotation of the optical deflection unit at a second speed higher than the first speed; and a driving controller configured to drive the optical deflection unit rotationally at the first speed upon detecting operation of the first switch and change the rotation speed of the optical deflection unit to the second speed upon detecting operation of the second switch, under a condition that the optical deflection unit rotates at the first speed when the second switch is operated.

According to one aspect, the optical tomographic diagnostic apparatus disclosed here is constructed in a way that makes it difficult for erroneous operation, relating to the rotation speed of the mirror portion inside the probe, to occur. The apparatus is also well suited to performing a scan superior in operability.

According to another aspect, an optical coherence tomographic image forming apparatus comprises: a light source which outputs light; an optical divider configured to divide light outputted from the light source into a measurement light and a reference light; an optical probe insertable inside a body lumen having biological tissue, the optical probe possessing a distal and portion at which is provided an optical deflection unit possessing an axis, the optical probe being configured to emit the measurement light toward the biological tissue which is reflected as reflected light and to receive the reflected light; a motor operatively connected to the optical deflection unit to rotate the optical deflection unit about the axis of the optical deflection unit at a first speed and a second speed higher than the first speed; a signal processing unit which receives information about light intensity of an interference light obtained from the reflected light and the reference light and uses said information to generate a cross-sectional image of the biological tissue inside the body lumen; and an operation unit operatively connected to the motor. The operation unit includes a first operating device which, upon operation, instructs the motor to rotate the optical deflection unit at the first speed, and a second operating device which, upon operation, instructs the motor to rotate the optical deflection unit at the second speed. A driving controller is configured to control the motor to rotationally drive the optical deflection unit at the first speed upon detecting operation of the first operating device, and to control the motor to rotationally drive the optical deflection unit at the second speed only when the second operating device is operated at a time when the optical deflection unit is rotating at the first speed.

Another aspect of the disclosure here involves a control method for an optical coherent tomographic image forming apparatus which divides light outputted from a light source into a measurement light and a reference light and generates a cross-sectional image of biological tissue in a body lumen based on light intensity of an interference light obtained from a reflected light produced by emitting the measurement light toward the biological tissue and the reference light while rotating an optical deflection unit located at a distal end portion of the optical probe positioned in the body lumen. The method comprises rotating the optical deflection unit at a first rotation speed greater than zero while the optical deflection unit is positioned in the living body lumen and while light is emitted from the optical deflection unit, and increasing the rotation speed of the optical deflection unit to a second rotation speed higher than the first rotation speed upon detecting that an operating device has been operated at a time when the optical deflection unit is rotating at the first rotation speed.

DETAILED DESCRIPTION

Hereinafter, in accordance with the attached drawings, an embodiment disclosed by way of example will be explained in detail.

[Explanation of Apparatus Structure and Operation]

First of all, it will be explained with respect to the structure of the overall apparatus and operation in this embodiment.

Figure 1:
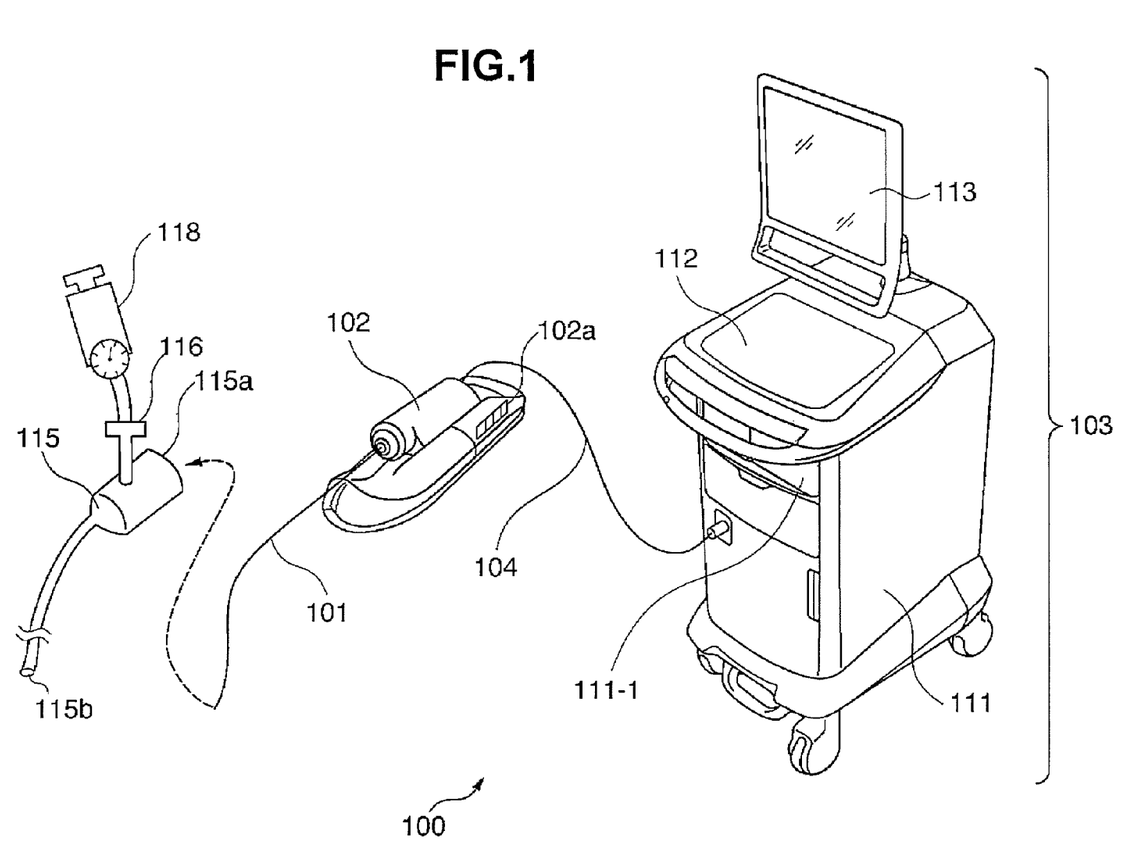
FIG. 1 is a diagram showing an outward-appearance constitution of an imaging apparatus for diagnosis relating to an embodiment disclosed by way of example.

FIG. 1 is a diagram showing a system constitution and an outward-appearance constitution of a wavelength sweep type optical coherence tomographic (OCT) image forming apparatus (hereinafter, referred to as imaging apparatus for diagnosis) equipped with the constitution of the embodiment. As shown in FIG. 1, the imaging apparatus for diagnosis 100 is provided with an optical probe unit 101, a scanner & pull-back unit 102 and an operation control apparatus 103.

Also, since a flush liquid described later is made to flow to a blood vessel region targeted for diagnosis, a guiding catheter 115 housing the optical probe unit 101 is used. An insertion hole, into which the optical probe unit 101 is inserted as shown by the arrow in FIG. 1, is provided at a rear end 115a of this guiding catheter 115 and an opening portion for exposing the optical probe unit 101 to the outside is provided at a distal end 115b. Then, this guiding catheter 115 is provided with a port 116 for connecting a medicine introducing portion 118 which accommodates the flush liquid described later. By operating this medicine introducing portion 118, the flush liquid accommodated in the inside is discharged through the distal end portion 11b.

The scanner & pull-back unit 102 and the operation control apparatus 103 are connected by the signal line & optical fiber 104. The guiding catheter 115 housing the optical probe unit 101 is directly inserted into a body lumen such as a blood vessel and the like, and the state inside the body lumen is measured by using an imaging core provided at a distal end of the optical probe unit 101. This optical probe unit 101 is constituted by an optical fiber 236 which passes through the inside thereof and a catheter sheath 403 which covers the outside thereof, and at least the vicinity of the distal end portion thereof is constituted by a transparent member (details thereof will be described later).

For the above-mentioned flush liquid, a physiological saline and a contrast agent (and a mixture liquid thereof) are used, and it is stored in the medicine introducing portion 118. The medicine introducing portion 118 is composed, for example, of a syringe, accommodates the flush liquid, and makes the flush liquid flow from a catheter distal end into a blood vessel by pressing a plunger thereof. By replacing the blood with the flush liquid after pushing and flowing away the blood, it become possible to make the scanning in a state in which the effect of the hematocyte component is less exerted.

Such an operation mentioned above is generally referred to as a flush operation, but the detail description thereof will be omitted here.

The scanner & pull-back unit 102 regulates a radial operation of an imaging core inside the optical probe unit 101 by rotational motion performed by a built-in motor. Also, this scanner & pull-back unit 102 performs an operation (pull-back process) for pulling back the optical fiber 236, which is rotating inside the optical probe unit 101, at a constant speed by driving another built-in motor. By this pull-back process, it is possible to obtain a continuous blood vessel tomographic image which is along the axis of a blood vessel. Also, this scanner & pull-back unit 102 is provided with an operation portion 102a which is arranged with various kinds of instruction switches for instructing the setting of the rotation speed, start/stop of the rotation and pullback of the optical fiber 236 inside the optical probe unit 101.

On an occasion when carrying out optical coherence tomographic image formation of biological tissue, the operation control apparatus 103 is provided with a function for inputting various kinds of setting values, a function for outputting measurement light, and a function for processing data obtained by measurement and displaying them as tomographic image. In the operation control apparatus 103, a reference numeral 111 indicates a main body control unit, which processes data obtained by measurement and outputs a processed result. A reference numeral 111-1 indicates a printer & DVD recorder and it happens that the processed result in the main body control unit 111 is printed and is stored as data. A reference numeral 112 indicates an operation panel and a user carries out inputs of various kinds of setting values and instruction through the operation panel 112. A reference numeral 113 indicates an LCD monitor as a display apparatus and it displays a processed result in the main body control unit 111.

Figure 2:
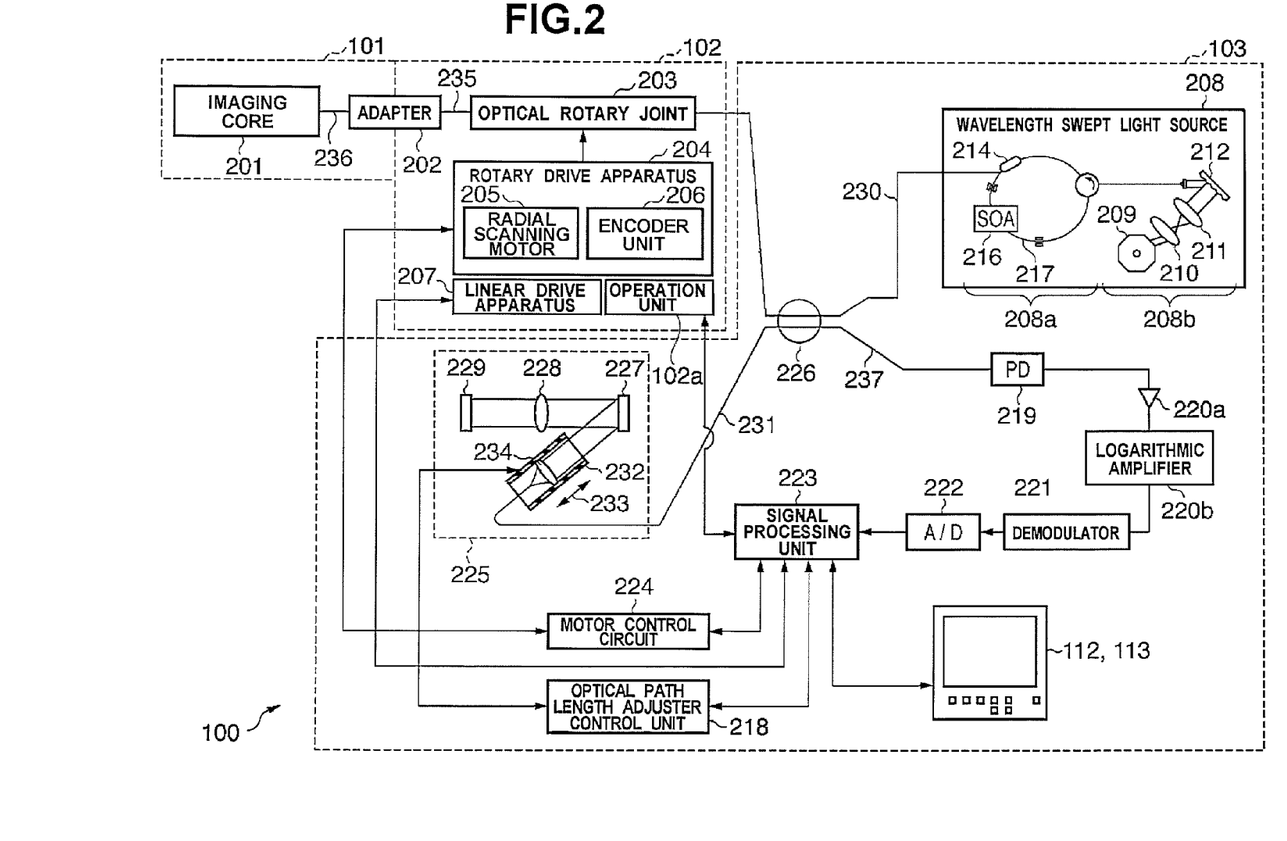
FIG. 2 is a block diagram showing a functional constitution of an imaging apparatus for diagnosis.

FIG. 2 is a functional constitution diagram of the imaging apparatus for diagnosis 100 shown in FIG. 1. In the drawing, a reference numeral 208 indicates a wavelength swept light source and a Swept Laser is used. The wavelength swept light source 208 is one kind of an Extended-cavity Laser which is composed of a light source portion 208a having an optical fiber 217 connected with an SOA216 (semiconductor optical amplifier) in a ring shape and a polygon scanning filter 208b. The light outputted from the SOA216 proceeds through the optical fiber 217 and enters the polygon scanning filter 208b and the light whose wavelength is selected here is amplified by the SOA216 and finally, is outputted from a coupler 214. In the polygon scanning filter 208b, the wavelength is selected depending on the combination of a diffraction grating 212 for light-splitting the light and a polygon mirror 209. The light which is light-split by the diffraction grating 212 is focused on the surface of the polygon mirror 209 depending on two lenses 210, 211. Thus, only the light of the wavelength perpendicular to the polygon mirror 209 returns to the same optical path and is outputted from the polygon scanning filter 208b, so that it is possible to carry out the time sweep of the wavelength by rotating the polygon mirror 209. For the polygon mirror 209, for example, a 72-facets mirror is used and the rotation speed thereof is around 50000 rpm. Owing to the unique wavelength sweep system in which the polygon mirror 209 and the diffraction grating 212 are combined, it is possible to employ the wavelength sweep of high speed and high power.

The light outputted from the coupler 214 of the wavelength swept light source 208 is made to enter one end of a first single mode fiber 230. The first single mode fiber 230 is guided to an optical coupler 226 which is optically coupled with a second single mode fiber 231 and here, the light is transmitted by being branched into two paths.

On the distal end side ahead of the photo coupler unit 226 of the first single mode fiber 230, there is provided a scanner & pull-back unit 102. Inside the scanner & pull-back unit 102, there is provided an optical rotary joint (optical coupling unit) 203 which connects between a non-rotary portion (fixed portion) and a rotary portion (rotationally drive portion) and which transmits the light. Further, a fourth single mode fiber 235 provided on the distal end side of the optical rotary joint 203 is connected in a freely detachable manner with a fifth single mode fiber 236 through an adapter 202. Thus, while repeating light transmission and reception, the light from the wavelength swept light source 208 is transmitted into an imaging core 201 which is rotationally driven.

The light transmitted to the fifth single mode fiber 236 is illuminated from the distal end side of the imaging core 201 with respect to a biological tissue of a blood vessel while performing radial operation. Then, a portion of the reflected light which is scattered on the surface of or in the inside of the biological tissue is taken-in by the imaging core 201 and returns to the first single mode fiber 230 side by way of the reverse optical path, and a portion thereof moves to the second single mode fiber 237 side by the photo coupler unit 226 which has functions as a light splitting unit and a light coupling unit at the same time. In the photo coupler unit 226, the reflected light is mixed with a reference light described below and is light-received as an interference light by a photo detector (in the embodiment disclosed by way of example, referred to as a photodiode, hereinafter as a PD) 219.

The rotation unit side of the optical rotary joint 203 is rotationally driven by a radial scanning motor 205 of the rotary drive apparatus 204. Also, the rotary angle of the radial scanning motor 205 is detected by an encoder unit 206. Further, the scanner & pull-back unit 102 is provided with a linear drive apparatus 207 and defines the insertion-direction (axial-direction) movement of the optical probe unit 101 based on an instruction from a signal processing unit 223. The axial-direction movement is realized by a mechanism in which a linear drive motor inside the linear drive apparatus 207 operates based on a control signal from the signal processing unit 223.

Also, there is provided a variable mechanism 225 of the optical path length for fine-adjusting the optical path length of the reference light at a distal end on the distal end side from the photo coupler unit 226 of the second single mode fiber 231. This variable mechanism 225 of this optical path length is provided with an optical path length adjuster for changing the optical path length which corresponds to the fluctuation of the length thereof such that the fluctuation of the length of the individual optical probe 201 can be absorbed in case of using the optical probe (imaging core) 201 by being exchanged. The second single mode fiber 231 and a collimator lens 234 are provided on a one-axis stage 232 which is freely movable in the optical axis direction thereof as shown by an arrow 233 and form the optical path length adjuster, More specifically, in case of exchanging the optical probe 201, the one-axis stage 232 functions as an optical path length adjuster having such an amount of variable range of optical path length, which can absorb the fluctuation of the optical path length of the optical probe. Further, the one-axis stage 232 is provided also with a function as an adjuster for adjusting an offset. For example, even in a case in which the distal end of the optical probe 201 is not closely attached to the surface of the biological tissue, minutely changing the optical path length by the one-axis stage makes it possible to set a state of interference from the surface position of the biological tissue.

The light reflected through mirrors 227, 229 and a lens 228 is inputted to a second single mode fiber 231 as the reference light. The reference light whose optical path length is fine-adjusted by the variable mechanism 225 of the optical path length is mixed with the reflected light from the first single mode fiber 230 side at the photo coupler unit 226 which is provided on the way of the second single mode fiber 231, and becomes the interference light, and it is light-received by the PD 219. The light which is light-received by the PD 219 is photoelectrically converted and becomes an electric signal, and it is inputted to an amplifier 220 and amplified, and thereafter, it is supplied to a demodulator 221. In this demodulator 221, a demodulation process for extracting only the signal component of the interference light is carried out and the output thereof is inputted to an A/D converter 222.

In the A/D converter 222, the interference light signal is applied with sampling, for example, by 180 MHz for 2048 points and digital data (interference data) of one line are generated. Note that the reason why the sampling frequency is set to be 180 MHz is on an assumption that about 90% of the period of wavelength sweep (12.5 µsec) is extracted as digital data of 2048 points in case of setting the repetition frequency of wavelength sweep to be 80 kHz and it is not limited by this aspect in particular.

The interference light data of one line unit, which are generated in the A/D converter 222 are inputted to the signal processing unit 223. In this signal processing unit 223, the interference light data are frequency-decomposed by FFT (Fast Fourier Transform) and data in the depth direction are generated, and by coordinate-converting these data, cross-sectional images at respective positions of the blood vessel are formed and outputted to an LCD monitor 113 by a predetermined frame rate.

Note that the signal processing unit 223 is connected with an optical path length adjuster control unit 218. The signal processing unit 223 carries out control of the position of the one-axis stage 232 by means of the optical path length adjuster control unit 218. Also, the signal processing unit 223 is connected with a motor control circuit 224 and in synchronization with a video synchronization signal when forming a cross-sectional image, the cross-sectional image is stored in an internal memory. In addition, the video synchronization signal of this motor control circuit 224 is transmitted also to the rotary drive apparatus 204 and in the rotary drive apparatus 204, a drive signal in synchronization with the video synchronization signal is outputted. Further, it happens that the signal processing unit 223 executes sampling of the interference light by the above-mentioned PD 219 and A/D converter 222.

Figure 4A:
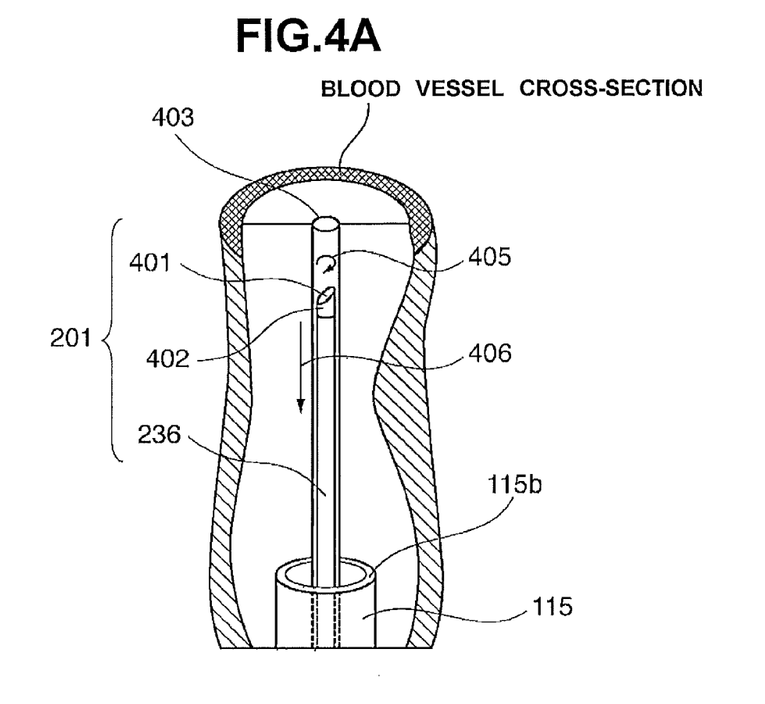
FIGS. 4A and 4B are diagrams explaining rotation scanning and axial-direction movement of an optical probe inside a blood vessel, and for explaining illumination of a measurement light and an intake of a reflected light.
Figure 4B:
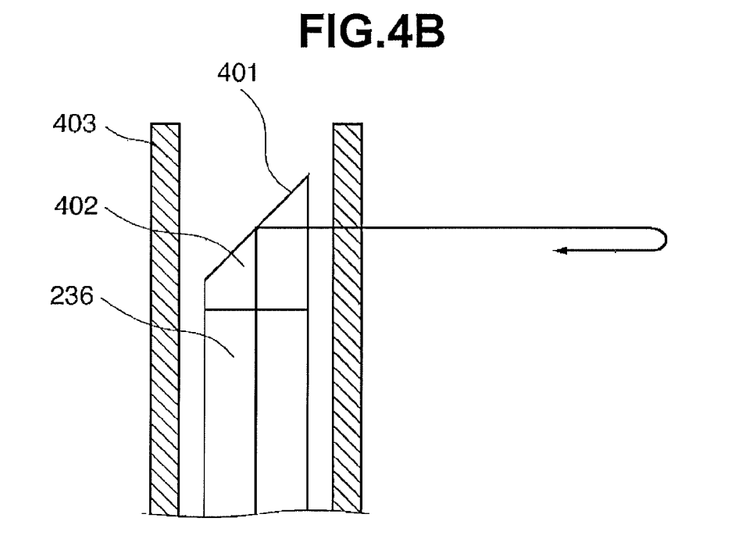

FIG. 4A is a diagram for explaining an aspect in which the imaging core 201 of the optical probe unit 101 is inserted into a body lumen (into a blood vessel) and a radial scan is carried out. A catheter sheath 403 installed with the imaging core 201 which is constituted by the optical fiber 236 including an optical mirror 401 and an optical lens 402 at the distal end thereof is inserted into, for example, a blood vessel lumen. The rotary drive apparatus 204 rotates the imaging core 201 in an arrow 405 direction in the inside of the catheter sheath 403 and the linear drive apparatus 207 moves it toward the arrow 406 direction (pull-back process). At that time, as shown in FIG. 4B, the measurement light from the wavelength swept light source 208 is illuminated to the blood vessel wall by the optical mirror 401 by way of the optical fiber 236. The reflected light to which the illuminated light is reflected is returned to the apparatus from the optical mirror 401 by way of the optical fiber 236. More specifically, the optical mirror 401 has a function as an optical deflection unit which deflects the axial direction light of the optical probe unit 101 from the optical fiber 236 toward or in the direction of the body lumen wall. For the optical deflection unit, also a prism or the like can be used.

Figure 5A:
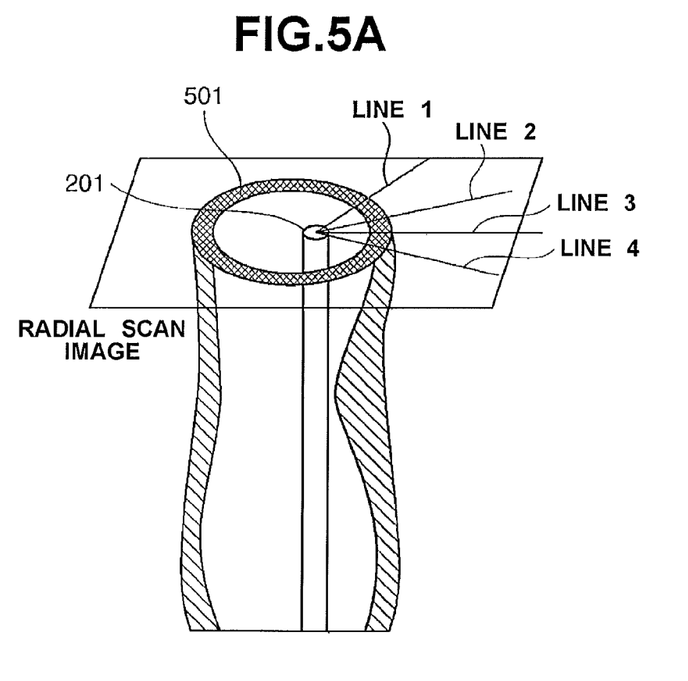
FIGS. 5A and 5B are schematic diagrams for explaining an operation of the optical probe inside the blood vessel.
Figure 5B:
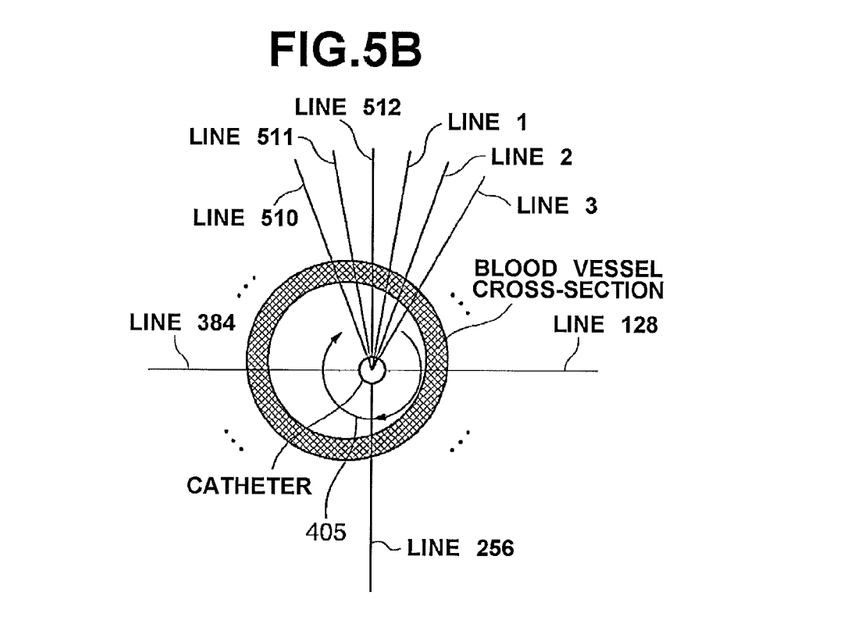

FIGS. 5A and 5b are schematic diagrams for explaining the operation of the optical probe unit 101 when imaging an intravascular tomographic image. FIGS. 5A and 5B are respectively a perspective view and a cross-sectional view of the blood vessel in a state in which the optical probe unit 101 is inserted thereinto. In FIG. 5A, a reference numeral 501 indicates a blood vessel cross-section into which the optical probe unit 101 is inserted. As described above, the imaging core 201 of the optical probe unit 101 is attached with the optical lens 402 and the optical mirror 401 at the distal end thereof and rotates in the direction shown by a reference numeral 405 in FIG. 5B depending on the radial scanning motor 205.

Depending on the optical lens 402, transmission & reception of the measurement light are carried out at respective rotary angles. Lines 1, 2, . . . , 512 show illumination directions of the measurement light at respective rotary angles. In this embodiment disclosed as an example, while the imaging core 201 including the optical mirror 401 and the optical lens 402 rotates as much as the angle of 360 degree at the position of a predetermined blood vessel cross-section 501, the transmission of measurement light & the reception of reflected light intermittently are carried out 512 times. Note that the number of times of the transmission & reception of the measurement light during a period of rotating 360 degrees is not limited by this aspect in particular and it is assumed that the number of times is settable arbitrarily. In this manner, the scan in which the transmission & reception of the signal is repeated while rotating the imaging core 201 is generally referred to as a "radial scan (rotation scan)". Also, the transmission of the measurement light & the reception of the reflected light by such an imaging core 201 is carried out while the imaging core 201 proceeds in the inside of the blood vessel toward the arrow 406 direction (see FIG. 4A).

Note that for the rotation speed of the imaging core 201 in the embodiment disclosed by way of example, there are provided two kinds of speeds of 1800 rpm and 9600 rpm. The 1800 rpm is a speed for mainly confirming whether or not the distal end portion of the imaging core 201 has been positioned at the aimed region and confirming whether or not the imaging core 201 is rotating correctly, and by this number of rotation, the pulling-back (pull-back) of the imaging core is not carried out toward the arrow 406 direction in FIG. 4A. Hereinafter, this rotation process by 1800 rpm is referred to as a process of a radial scan mode.

On the other hand, the 9600 rpm is a speed for obtaining a high-resolution blood vessel tomographic image and also, is a mode for obtaining an image in a predetermined range along the blood vessel axis. Accordingly, in this mode, the process of pull-back toward the arrow 406 direction in FIG. 4A is carried out while rotating the imaging core 201 by 9600 rpm. The flush operation explained previously (operation of injecting flush liquid) is carried out in this case. Hereinafter, this mode is referred to as a pull-back scan mode. The arrow 406 in FIG. 4A is the direction toward which the imaging core 201 is pulled back and it is opposite to the direction toward which the blood flows. When the flush operation is carried out, the medicine is outpoured toward the inside of the blood vessel from the distal end portion 115b of the guiding catheter 115 by passing through the empty space between the guiding catheter 115 and the catheter sheath 403, and at the portion thereof, the blood is drifted away and replaced by the medicine in which a flow without having an influence of the hematocyte component is produced. Then, during the pull-back operation, the distal end portion of the imaging core 201 moves in the area replaced by the medicine toward the arrow 406 direction and it become possible to scan for a highly accurate image. During the pull-back, the guiding catheter 115 is arranged at a position so as not to cover the distal end portion of the imaging core 201.

Figure 3:
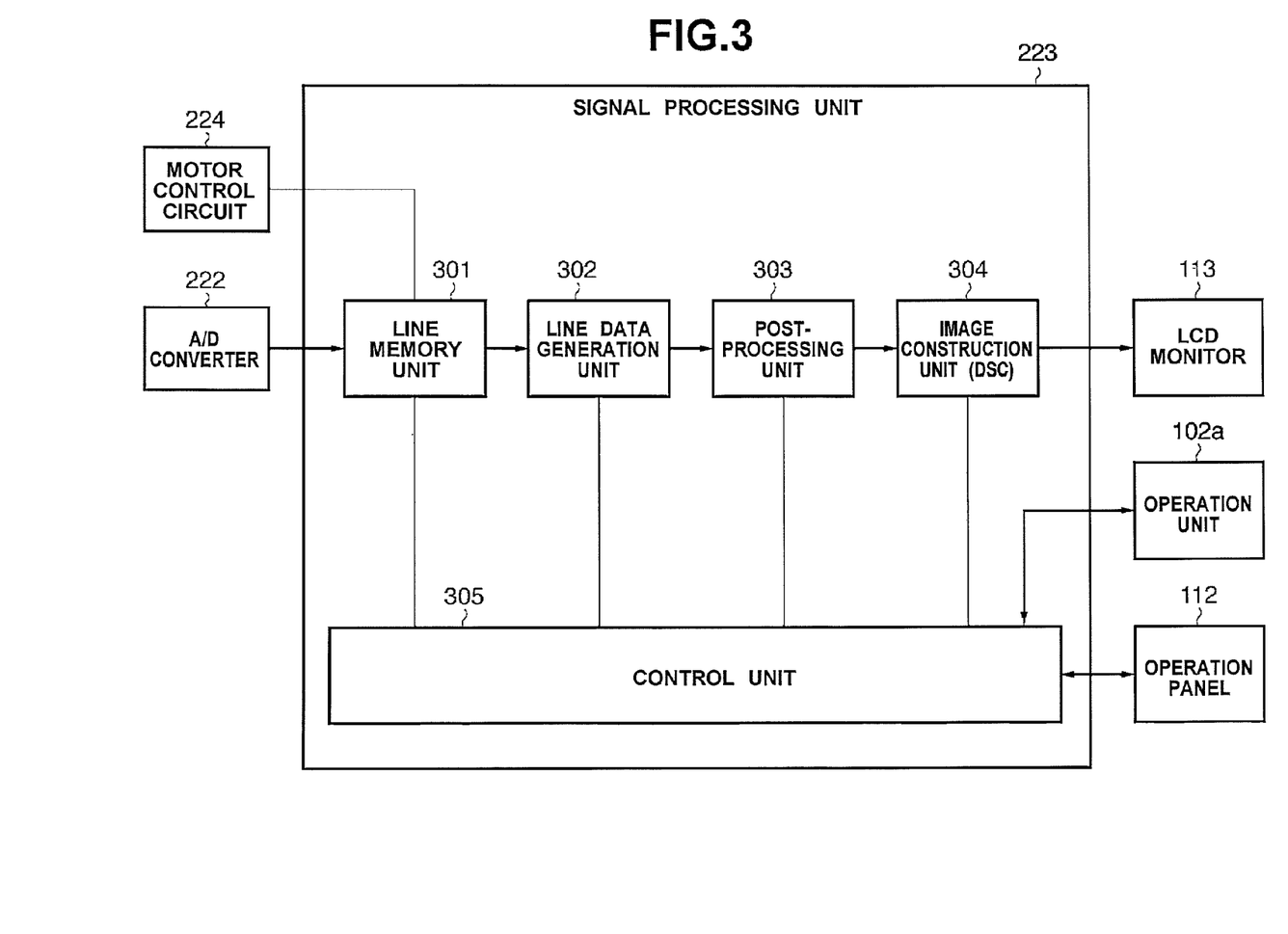
FIG. 3 is a block diagram showing a functional constitution of a signal processing unit.

FIG. 3 shows a constitution of a signal processing unit 223 in the embodiment disclosed by way of example. This signal processing unit 223 carries out a generation process of the tomographic image based on an electric signal (signal from A/D converter 222) obtained from the interference light in the radial scan mode and the pull-back scan mode which are mentioned above in accordance with an instruction by an operator depending on the operation panel 112 and the operation unit 102a. This generation process will be explained next.

The signal processing unit 223 stores data of the interference light for one line by the wavelength sweep from the A/D converter 222 sequentially into a line memory unit 301. Then, depending on an encoder signal of the motor, which is outputted from a motor control circuit 224, signals are selected and grouped such that the number of lines per one rotation of the motor becomes 512 lines. More specifically, the interference light data per one line are outputted to the line data generation unit 302 by every 512 data per one rotation of the motor.

The line data generation unit 302 generates the line data by carrying out an FFT (Fast Fourier Transform) process and concurrently, a line addition-averaging process, a filtering process, a logarithmic conversion and the like are carried out, and the obtained line data are outputted to a post-processing unit 303 at a subsequent stage. The line data is defined as data array which makes a line from center of the cross-sectional image to edge of the cross-sectional image. The line date is produced from coherence light intensity of the emission direction of the transmitting.

In the post-processing unit 303, a contrast adjustment, a brightness adjustment, a gamma correction, a frame correlation, a sharpness process and the like are applied for the line data received from the line data generation unit 302, and the processed result thereof is outputted to an image construction unit 304. The image construction unit 304 converts the line data train of polar-coordinate to a video signal and displays it on the LCD monitor 113 as blood vessel cross-sectional images. Note that as one example, there is shown, here, an example of constructing an image by 512 lines, but it is not to be limited by this number of lines. It happens that a control unit 305 controls a series of operations of the respective units mentioned above, but the contents of calculation until the blood vessel tomographic image is obtained and portions relating to the display process thereof do not directly concern the embodiment, so that further detailed explanations will be omitted.

[Explanation of User Interface]

Next, it will be explained with respect to user interface for an operator in the embodiment disclosed by way of example. First, before moving to an explanation of the user interface, set forth will be an explanation of premise or peripherally related portions.

As explained previously, for the scan mode in this example of an embodiment, there are the radial scan mode (process for making the optical mirror 401 rotate by 1800 rpm) and the pull-back scan mode (pull-back process of the optical fiber 236 in which the optical mirror 401 is rotated by 9600 rpm and the optical mirror 401 is made to move by a constant speed toward the arrow 406 direction in FIG. 4).

Problems are not caused by rotation at 1800 rpm, but when the optical fiber 236 (optical mirror 401) is rotated in the catheter sheath by a high speed such as 9600 rpm, frictional heat is generated there and it happens that the temperature of the catheter sheath will heighten or increase. Therefore, it is not desirable for the biological tissue on the outside of the catheter sheath to continue the rotation (high speed rotation) for a long period. In addition, there also occurs a possibility which leads to breakages of the optical fiber 236 and the optical mirror 401. Consequently, it was required to set the duration time of the rotation speed referred to as 9600 rpm to be within 42 seconds maximally and more specifically, to provide a limiter for the duration time of the high speed rotation of the pull-back scan mode.

However, in a case in which it happens that the operator instructs the high speed rotation by 9600 rpm caused by an erroneous operation and it happens that the pull-back scan is instructed without being aware of a fact that the high speed rotation thereof continues nearly for 42 seconds, it happens that the duration time terminates on the way of the scan and the rotation stops, so that complete measurement data cannot be obtained. Therefore, it is necessary to prevent such an erroneous operation as much as possible. Note that the above-mentioned 42 seconds as the maximum duration time is merely presented as one example and it is a value which is suitably changeable.

Also, as explained previously, the pull-back scan mode is a mode in which the tomographic image of a predetermined distance of the blood vessel is scanned while carrying out the pull-back of the optical fiber, so that it is necessary to provide time for achieving the movement over the predetermined distance until the scan is completed. Therefore, the timing for starting the pull-back process has to be set within a time period which is obtained by subtracting as much as an amount of time necessary for the pull-back process thereof from the maximum duration time (42 seconds) by 9600 rpm. Although depending on the length of the scan, in this embodiment disclosed by way of example, it is assumed that the rotation is to be stopped if the start instruction of the pull-back process is not carried out within 30 seconds after the rotation speed becomes 9600 rpm.

Figure 6:
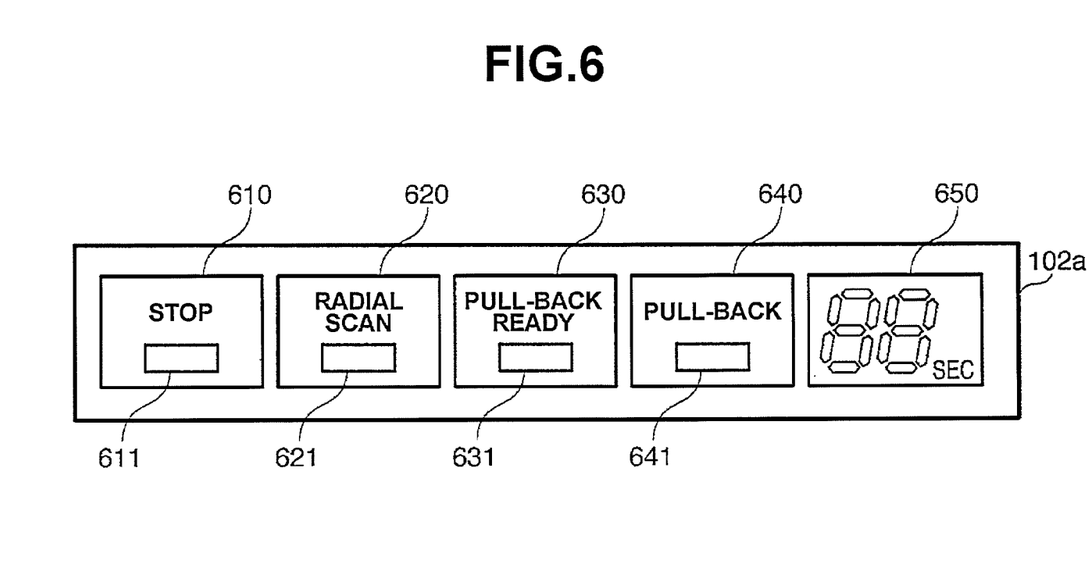
FIG. 6 is a diagram showing an operation unit of a scanner & pull-back unit.
Figure 7:
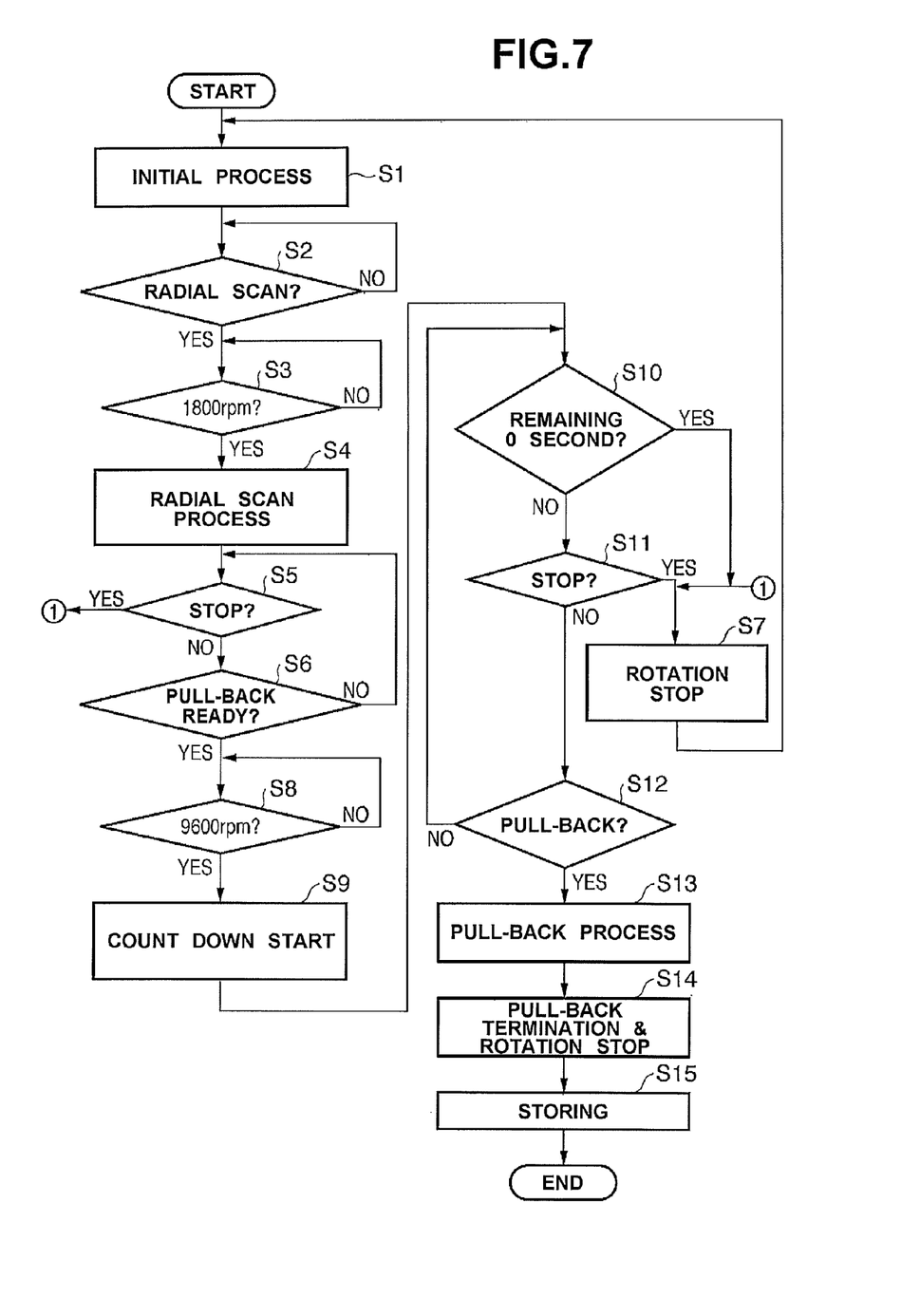
FIG. 7 is a flowchart showing a process procedure of a signal processing unit with respect to an operation by the operation unit of the scanner & pull-back unit.

In light of the foregoing, according to FIG. 6 showing one example of the operation unit 102a in the scanner & pull-back unit 102 and FIG. 7 showing a process procedure, there will be explained processes (process contents of the signal processing unit 223) relating to the user interface in an embodiment.

As shown in FIG. 6, in the operation unit 102a provided at the scanner & pull-back unit 102, there are provided a switch 610 for stopping the rotation of the optical fiber 236, a switch 620 for instructing a shifting to the radial scan mode (1800 rpm), a switch 630 for instructing an entering to the pull-back scan mode and a shifting to a state in which the pull-back is possible (9600 rpm), and a switch 640 for carrying out a start instruction of the pull-back. The switches (inclusive of buttons which are also acceptable) are examples of operating devices for initiating the respective noted operations. Also, those switches are installed with LEDs 611, 621, 631, 641 as lighting display devices for notifying the states of the switches respectively. The relationships between driving states of the LEDs and functional states of the switches are as follows.

LED turned off: Indicating a state in which the function of the switch thereof is not expressed LED turned on: Indicating a state in which the function of the switch thereof is expressed LED blinking: Indicating a transitional state until the function of the switch thereof is expressed Since it is enough if only the state can be distinguished, it is possible to employ another driving method than the driving method for the LEDs, which was mentioned above. Depending on the case, it is possible to prepare LEDs having a number of light-emitting colors and to change the light-emitting colors in response to the state.

Also, the operation unit 102a is provided with a display unit 650 for countdown-displaying the remaining number of seconds during which the pull-back switch 640 can be pushed down when the rotation becomes 9600 rpm.

Hereinafter, there will be explained processes of the signal processing unit 223 in an embodiment disclosed by way of example in accordance with a flowchart in FIG. 7.

First, the signal processing unit 223 carries out, in step S1, an initial process of each constituent element used for an optical coherence tomographic image formation process. Within this process, there are included a turn-on process of the LED 621 for notifying the fact that the radial scan switch 620 functions, and turn-off processes of the LEDs 611, 631, 641 for notifying the fact that other switches do not function. It becomes a situation in which the operator carries out, in this state, an operation for guiding the optical probe unit 101 to the inside of the blood vessel in the diagnosis region of a patient.

The operator pushes down the radial scan switch 620 in order to confirm the position of the optical probe 201, to fine-adjust the position and to confirm whether or not the optical mirror portion 401 rotates normally. When the signal processing unit 223 detects the push-down of this radial scan switch 620 ("Yes" in step S2), the driving of the radial scanning motor 205 is carried out for making the optical fiber 236 rotate by 1800 rpm. At that time, the LED of the radial switch 620 is put into a blinking state. Note that even if a switch other than the radial scan switch 620 within the switch group shown in FIG. 6 is pushed down, that is ignored. The configuration in which the push-down of a switch lying in a turned-off state is ignored will be similar also in the explanation hereinafter.

Then, in step S3, when it is judged that the speed has reached 1800 rpm, there is carried out a process for obtaining the tomographic image at the rotation speed thereof and there is carried out a process for displaying the image thereof on the LCD monitor 113 (step S4). As a result thereof, it is possible for the operator to confirm and fine-adjust the position of the optical mirror portion 401 and confirm whether or not the optical mirror portion 401 rotates normally. In this situation, in order to obtain a more accurate image, it sometimes happens that the operator carries out a flush operation using a small amount of medicine (operation of making the medicine at the medicine introducing portion 120 flow out from the distal end portion 115b of the guiding catheter 115). Also, in the course of carrying out the process of this step S4, the LEDs 611, 631 are turned on, thus providing notification that the push-downs of the stop switch 610 and the pull-back ready switch 630 are to be regarded as effective, and the system then waits for the detection of the push-down of any one of the switches (steps S5, S6).

Here, when the push-down of the stop switch 610 is detected, the signal processing unit 223 stops the rotation of the optical fiber 236 in step S7 and the process is returned to step S1.

On the other hand, when the push-down of the pull-back ready switch 630 is detected, the signal processing unit 223 carries out the driving of the radial scanning motor 205 in order to rotate the optical fiber 236 by 9600 rpm and concurrently, blinks the LED 631 (step S6). Then, in step S8, the system waits until the rotation speed reaches 9600 rpm.

When the speed reaches 9600 rpm, it becomes a state in which the pullback is possible, there is started the countdown of the residual time (30 seconds in the embodiment) until it is no longer possible to carry out the pullback, and there is started displaying of the residual time thereof on the display unit 650 (step S9). During this countdown, the switches which the operator can operate are the stop switch 610 and the pull-back switch 640, so that the respective LEDs 611, 641 are turned on and the LEDs 621, 631 of the other switches are turned off.

The signal processing unit 223 judges whether or not the remaining number of seconds by the countdown is zero second in step S10 and whether or not any one of the stop switch 610 and the pull-back switch 640 has been pushed down in steps S11, S12, and looping takes place in S10 to S12 until any one is judged. Note that if the speed is allowed to return to 1800 rpm, it is allowed during this looping to turn on the LED 621, to carry out a process of judging whether or not the radial scan switch 620 has been pushed down and to return the process to step S3 when the push-down thereof is detected.

Now, in the looping mentioned above, in a case in which the remaining number of seconds by the countdown has become zero second or the push-down of the stop switch 611 has been detected, the process proceeds to step S7, stops the rotation of the optical fiber 236 and returns to step S1. At that time, the LED 641 is turned off.

On the other hand, when the push-down of the pull-back switch 640 is detected (at that time, operator is carrying out flush operation for introducing medicine into a blood vessel from medicine introducing portion 118), the process proceeds to step S13. Here, the signal processing unit 223 starts driving of the linear drive apparatus 207 and carries out the process of pulling the optical fiber 236 (rotating at 9600 rpm) by a predetermined speed as much as a distance which is set beforehand. During that period, as explained previously, there is carried out the sampling of the electric signal of the interference light by the A/D converter 222 and there is carried out the process for obtaining the three-dimensional tomographic images of the blood vessel. During this pull-back process, the LED 641 of the pull-back switch 640 is blinking and the LEDs of the other switches are turned off. In this manner, when the pull-back of the optical fiber 236 for the necessary distance is finished, the process proceeds to step S14, the process of the pull-back is terminated and the rotation of the optical fiber 236 is stopped. At that time, all of the LEDs are turned off. Thereafter, the process proceeds to step S15 and information such as the obtained interference light data and the like is stored in a memory unit of a hard disk or the like which is not shown, and this process is finished.

As explained above, according to this embodiment, it is not possible to shift to such a high-speed rotation as 9600 rpm without undergoing such a low-speed rotation as 1800 rpm for carrying out the confirmation operation, so that in a non-rotation state, even if the pull-back ready switch is pushed down by an erroneous operation, it is possible to treat the operation thereof as invalid and it become possible to improve safety and operability. Also, there can be obtained a situation in which whether or not each switch is effective can be confirmed by the driving state of the LED provided at each switch and it becomes more possible to prevent erroneous operations. Note that to provide the stage of such a low-speed rotation as 1800 rpm is useful for carrying out various kinds of the confirmation operations for which high-speed rotation is not required, and it becomes effective in case of avoiding heat generation and breakdown.

Note that in the embodiment, an example was explained in which each switch is arranged at the scanner & pull-back unit 102. Instead of or in addition to this aspect, it is also allowed for a similar switch to be provided at the operation panel 112 or to be displayed on the LCD monitor 113.

Also, in the embodiment disclosed by way of example embodiment, examples of 1800 rpm and 9600 rpm were explained for the rotation speeds of the optical fiber 236, but the present invention is not to be limited by these rotation numbers. It is needless to say that the length of time for counting down also varies depending on the apparatus constitution and/or the setting, so that the present invention is not to be limited by the embodiments mentioned above.

The detailed description above describes features and aspects of an embodiment of an optical coherence tomographic image forming apparatus and associated control method disclosed by way of example. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An optical coherence tomographic image forming apparatus comprising:
   a light source which outputs light;
   an optical divider configured to divide light outputted from the light source into a measurement light and a reference light;
   an optical probe insertable inside a body lumen having biological tissue, the optical probe possessing a distal and portion at which is provided an optical deflection unit possessing an axis, the optical probe being configured to emit the measurement light toward the biological tissue which is reflected as reflected light and to receive the reflected light;
   a motor operatively connected to the optical deflection unit to rotate the optical deflection unit about the axis of the optical deflection unit at a first speed and a second speed higher than the first speed;
   a signal processing unit which receives information about light intensity of an interference light obtained from the reflected light and the reference light and uses said information to generate a cross-sectional image of the biological tissue inside the body lumen;
   an operation unit operatively connected to the motor and comprising a first operating device which, upon operation, instructs the motor to rotate the optical deflection unit at the first speed, and a second operating device which, upon operation, instructs the motor to rotate the optical deflection unit at the second speed;
   a driving controller configured to control the motor to rotationally drive the optical deflection unit at the first speed upon detecting operation of the first operating device, and to control the motor to rotationally drive the optical deflection unit at the second speed only when the second operating device is operated at a time when the optical deflection unit is rotating at the first speed;
   a time counter which measures a time period, beginning when the rotation speed of the optical deflection unit reaches the second speed, during which the optical deflection unit continues rotating at the second speed; and
   a rotation stopper which stops the rotation of the optical deflection unit when the time period measured by the time counter reaches a preset time greater than zero
   a third operating device which, upon operation, instructs movement of the optical deflection unit at a predetermined speed along the axial direction of the optical probe; and
   a movement controller for moving the optical deflection unit at the predetermined speed, upon detecting operation of the third operating device at a time when the optical deflection unit is rotating at the second speed; and
   a countdown display device which displays a residual time until a time limit within which the third operating device must be operated to complete the movement of the optical deflection unit at the predetermined speed after the optical deflection unit reaches the second speed.

2. The optical coherence tomographic image forming apparatus according to claim 1, wherein the first operating device, the second operating device and the third operating device are each provided with a respective lighting display device for notifying whether or not operation of the respective operating device is effective.

3. The optical coherence tomographic image forming apparatus according to claim 1, wherein the first operating device and the second operating device include lighting display devices each configured to be in a first state indicating that operation of the operating device will not be effective and a second state indicating that operation of the operating device will be effective.

* * * * *